US008840671B2

(12) United States Patent
Ambacher

(10) Patent No.: US 8,840,671 B2
(45) Date of Patent: *Sep. 23, 2014

(54) SHOULDER PROSTHESIS

(75) Inventor: Thomas Ambacher, Pforzheim (DE)

(73) Assignee: Zimmer GmbH, Winterthur (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/428,441

(22) Filed: Mar. 23, 2012

(65) Prior Publication Data

US 2012/0296435 A1    Nov. 22, 2012

(30) Foreign Application Priority Data

Mar. 25, 2011 (EP) .................................... 11002505
Feb. 15, 2012 (EP) .................................... 12155644

(51) Int. Cl.
*A61F 2/40* (2006.01)

(52) U.S. Cl.
USPC .................................... 623/19.11; 623/19.14

(58) Field of Classification Search
USPC .......... 623/19.11, 19.13, 19.14, 22.23, 22.32, 623/22.38, 23.11, 23.12, 23.14, 23.42, 623/23.43

See application file for complete search history.

(56) References Cited

U.S. PATENT DOCUMENTS

| 4,035,848 A | 7/1977 | Wagner |
| 4,042,980 A | 8/1977 | Swanson et al. |
| 4,332,036 A * | 6/1982 | Sutter et al. ................. 623/23.42 |
| 4,470,158 A | 9/1984 | Pappas et al. |
| 4,550,450 A | 11/1985 | Kinnett |
| 4,964,865 A | 10/1990 | Burkhead et al. |
| 4,986,833 A | 1/1991 | Worland |
| 5,032,132 A | 7/1991 | Matsen, III et al. |
| 5,250,050 A | 10/1993 | Poggie et al. |
| 5,271,737 A | 12/1993 | Baldwin et al. |
| 5,314,479 A | 5/1994 | Rockwood, Jr. et al. |
| 5,358,526 A | 10/1994 | Tornier |
| 5,403,320 A | 4/1995 | Luman et al. |
| 5,489,309 A | 2/1996 | Lackey et al. |
| 5,571,203 A | 11/1996 | Masini |
| 5,665,090 A | 9/1997 | Rockwood et al. |

(Continued)

FOREIGN PATENT DOCUMENTS

| DE | 1164019 B | 2/1964 |
| DE | 19803183 A1 | 8/1999 |

(Continued)

OTHER PUBLICATIONS

European Search Report mailed May 2, 2012 in European Patent Application No. EP12155644.3.

(Continued)

*Primary Examiner* — Randy Shay
(74) *Attorney, Agent, or Firm* — Schwegman Lundberg & Woessner, P.A.

(57) ABSTRACT

The present disclosure relates to a stemless shoulder prosthesis comprising a fixation device for fixing the prosthesis to a resected humerus bone, the fixation device comprising a base portion and anchoring means, the base portion having a distal side adapted to contact a resection plane of the bone and a proximal side for carrying a humeral head. The anchoring means are connected to the distal side of the base portion and adapted to fix the prosthesis to the bone. The anchoring means define a central axis perpendicular to the distal side of the base portion and a free central space around the central axis.

11 Claims, 2 Drawing Sheets

(56) References Cited

U.S. PATENT DOCUMENTS

Figure 1:
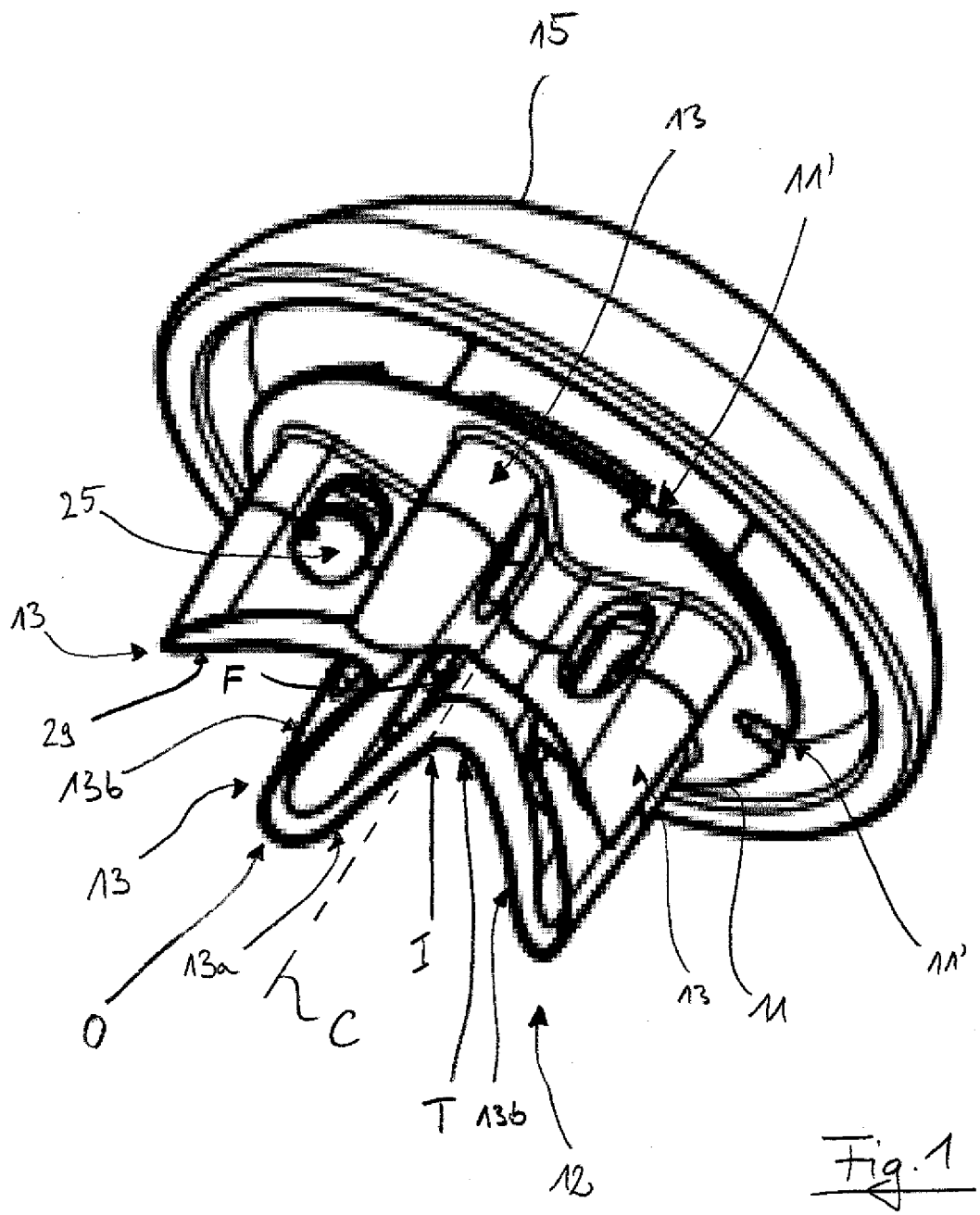

| | | | |
|---|---|---|---|
| 5,957,979 | A | 9/1999 | Beckman et al. |
| 6,146,423 | A | 11/2000 | Cohen et al. |
| 6,168,630 | B1 | 1/2001 | Keller et al. |
| 6,783,549 | B1 * | 8/2004 | Stone et al. ............... 623/19.14 |
| 7,465,319 | B2 | 12/2008 | Tornier |
| 7,615,080 | B2 | 11/2009 | Ondrla |
| 7,670,382 | B2 | 3/2010 | Parrott et al. |
| 7,678,150 | B2 | 3/2010 | Tornier et al. |
| 7,887,544 | B2 | 2/2011 | Tornier et al. |
| D643,926 | S | 8/2011 | Collins |
| 8,187,282 | B2 | 5/2012 | Tornier et al. |
| 8,192,497 | B2 | 6/2012 | Ondrla |
| 8,231,682 | B2 | 7/2012 | Lafosse et al. |
| 8,246,687 | B2 | 8/2012 | Katrana et al. |
| 2001/0047210 | A1 * | 11/2001 | Wolf ........................... 623/19.14 |
| 2003/0028253 | A1 | 2/2003 | Stone et al. |
| 2003/0153918 | A1 | 8/2003 | Putnam et al. |
| 2007/0142917 | A1 * | 6/2007 | Roche et al. ............... 623/19.11 |
| 2007/0162149 | A1 * | 7/2007 | Kropf et al. ................ 623/23.42 |
| 2008/0221700 | A1 * | 9/2008 | Howald et al. ............. 623/23.12 |
| 2009/0048681 | A1 * | 2/2009 | Vlachos ...................... 623/23.12 |
| 2010/0114326 | A1 * | 5/2010 | Winslow et al. ........... 623/23.42 |
| 2012/0265315 | A1 * | 10/2012 | Kusogullari et al. ...... 623/19.14 |

FOREIGN PATENT DOCUMENTS

| | | |
|---|---|---|
| EP | 0013864 A1 | 8/1980 |
| EP | 0485326 A1 | 5/1992 |
| EP | 0577529 A1 | 1/1994 |
| EP | 1467681 B1 | 2/2008 |
| FR | 2304324 A1 | 10/1976 |
| FR | 2691355 A1 | 11/1993 |
| WO | WO02/17822 A1 | 3/2002 |
| WO | WO2007/054553 A1 | 5/2007 |
| WO | WO-2012130524 A1 | 10/2012 |

OTHER PUBLICATIONS

"U.S. Appl. No. 13/428,446, Advisory Action mailed Oct. 7, 2013", 2 pgs.

"U.S. Appl. No. 13/428,446, Examiner Interview Summary mailed Jul. 23, 2013", 3 pgs.

"U.S. Appl. No. 13/428,446, Final Office Action mailed Jul. 25, 2013", 9 pgs.

"U.S. Appl. No. 13/428,446, Non Final Office Action mailed Dec. 28, 2012", 10 pgs.

"U.S. Appl. No. 13/428,446, Preliminary Amendment filed Mar. 23, 2012", 5 pgs.

"U.S. Appl. No. 13/428,446, Response filed Jun. 28, 2013 to Non Final Office Action mailed Dec. 28, 2012", 3 pgs.

"U.S. Appl. No. 13/428,446, Response filed Sep. 25, 2013 to Final Office Action mailed Jul. 25, 2013", 7 pgs.

"U.S. Appl. No. 29/413,610, Restriction Requirement mailed Oct. 4, 2013", 7 pgs.

"U.S. Appl. No. 29/413,611, Restriction Requirement mailed Oct. 4, 2013", 7 pgs.

"European Application Serial No. 12155645.0, European Search Report mailed May 2, 2012", 4 pgs.

"International Application Serial No. PCT/EP2012/052627, International Search Report and Written Opinion mailed May 4, 2012", 5 pgs.

"U.S. Appl. No. 13/428,446, Non Final Office Action mailed Nov. 1, 2013", 8 pgs.

"U.S. Appl. No. 29/413,611, Response filed Nov. 4, 2013 to Restriction Requirement mailed Oct. 4. 2013", 8 pgs.

"U.S. Appl. No. 29/413,610, Non Final Office Action mailed Dec. 20, 2013", 7 pgs.

"U.S. Appl. No. 29/413,610, Response filed Nov. 4, 2013 to Restriction Requirement mailed Oct. 4, 2013", 9 pgs.

"U.S. Appl. No. 29/413,611, Non Final Office Action mailed Dec. 19, 2013", 7 pgs.

"International Application Serial No. PCT/EP2012/052627, International Preliminary Report on Patentability mailed Mar. 8, 2013", 11 pgs.

* cited by examiner

SHOULDER PROSTHESIS

The present disclosure relates to a stemless shoulder prosthesis.

Generally, a stemless shoulder prosthesis comprises a metaphysical fixation device for fixing the prosthesis to a resected humerus bone. The fixation device comprises a base portion and anchoring means, with a humeral head being fixed to the base portion, for example through a taper or screw connection.

Unlike shoulder prostheses having a stem, also referred to as stemmed shoulder prostheses, stemless shoulder prostheses do not make use of the humeral canal in the diaphysis of the humerus. In other words, stemless shoulder prostheses do not rely on their fixation in said canal and an anchoring means extending deep into said canal is therefore not provided. This bears the advantage that it is in general not necessary to prepare the humeral canal for the insertion of the prosthesis and consequently bone is preserved.

In EP 1 467 681 a shoulder joint endoprosthesis is disclosed which, while fixation is largely limited to the epiphyseal region of the humerus, relies on a short central stem for fixation within the bone. Any ribs or fins solely are described as a torsional safeguard while fixation is achieved through a short tapered stem.

The present disclosure relates to a stemless shoulder prosthesis having a specifically designed fixation device. In particular, combinations of specific base portion designs and anchoring means are described.

According to the present disclosure, the base portion has a distal side adapted to contact a resection plane of the bone and a proximal side for carrying a humeral head. The anchoring means are connected to the distal side of the base portion and adapted to fix the prosthesis to the bone. The anchoring means define a central axis perpendicular to the distal side of the base portion and a free central space around the central axis. The anchoring means comprise wall sections projecting from the base portion substantially perpendicular to the distal side of the base portion, wherein each wall section extends between an inner edge and an outer edge. The wall sections have a height measured from the distal side of the base portion, the height of each wall section decreasing from its outer edge towards the inner edge, each wall section having a maximum height at its outer edge and a minimum height at its inner edge.

In other words, said free central space is not provided with protrusions or stem-like anchoring means. In an implanted state of the prosthesis, bony material of the humerus bone can penetrate the free central space and contribute to the anchoring of the prosthesis in the bone.

The wall sections stabilize and fix the prosthesis to the bone in an implanted state of the prosthesis. The design of the wall sections—which may be essentially planar or comprise curved segments—having decreasing heights towards the central axis result—in a side view of the prosthesis—in a shape resembling in essence an inverted arrow. Said design yields a reliable fixation of the prosthesis to the bone and minimizes the impact on the radially inner bone material.

In this context, the terms "inner edge" and "outer edge" are to be understood such that the "inner edge" has a smaller distance from the central axis than the corresponding "outer edge". The wall sections may extend not exclusively in a radial direction but may have an extension component in a circumferential direction, may be curved or may extend in a linear, non-radial direction.

In an embodiment of the prosthesis according to the present disclosure, the wall sections may be arranged around the free central space and are in particular evenly distributed.

In a further embodiment of the prosthesis according to the present disclosure, the wall sections form a wall extending around the free central space. In particular, the wall extends around the free central space in a closed loop. Thereby, a closed wall without circumferential free ends enclosing the free central space may be formed. The wall may define alternating radially outer convex wall portions and radially inner concave wall portions as the wall extends around the free central space.

In principle, the geometry defined by the wall sections may be chosen in accordance with the individual needs of the specific patient. Exemplarily, the wall has a star-shape when viewed along the central axis towards the base portion.

In an embodiment of the prosthesis according to the present disclosure, the outer edge of each wall section is rounded.

In a further embodiment of the prosthesis according to the present disclosure, each wall section is formed by two wall portions merging into one another at the outer edge of the wall section and each wall portion of a wall section merging into a wall portion of a neighboring wall section at a common transition zone. The wall portions of each wall section may extend at least partially parallel to each other. In other words, the wall portions at least in part do not diverge or converge in a projection on a plane defined by the base portion. Additionally or alternatively, each transition zone—where neighboring wall sections merge—may be rounded.

In a further embodiment of the prosthesis according to the present disclosure, each wall section may have its minimum height at the common transition zone.

To facilitate the insertion of the prosthesis into the humerus bone, each wall section may comprise a distal edge which is formed at least partly as a cutting edge.

To improve the osseointegration of the prosthesis and blood supply of the bone, at least one of the wall sections may comprise at least one opening.

In an embodiment of the prosthesis according to the present disclosure, the base portion comprises a plate which may optionally be provided with openings and/or recesses.

The outer contour of the base portion may have a circular shape. Alternatively, the base portion may be given an anatomical design which is different from a circular shape. Specifically, the base portion may be given a substantially egg-shaped or pear-shaped design.

Regarding the circumferential direction around the central axis, the wall sections are in specific embodiments arranged at regular intervals. For example, in a design relying on four wall sections, the wall sections may be arranged at 90° between every two neighboring wall sections. Generally, a symmetrical design, in particular if combined with a circular base portion, may be found advantageous.

Alternatively, the wall section may be arranged asymmetrically in the circumferential direction. Such an anatomical design, in particular if combined with a non-circular design of the base portion, may make use of specific anatomical provisions given at the resected humerus bone.

Specifically, it may be taken into account that the bone material below the resection plane does not exhibit a constant bone depth or bone density. Moreover, such an anatomical design may account for the fact that the cross-sections of the resection plane have no symmetry planes.

The number and/or the positioning of the wall sections in such an anatomical design may be chosen in consideration of the mentioned anatomical circumstances in order to obtain reliable support and stability for the prosthesis. The design may or may not be chosen such that the prosthesis is supported predominantly by the cortical bone. Moreover, an anatomical design makes it possible to maximize the cortical coverage for the prosthesis.

Generally, the stemless shoulder prosthesis as disclosed herein may be used in total shoulder arthroplasty as well as in hemi shoulder arthroplasty. Moreover, the disclosed shoulder prosthesis may be used for patients with a so-called dysfunctional rotor cuff.

In addition, the stemless shoulder prosthesis as disclosed herein provides for the general advantages over stemmed prostheses, namely to preserve more bone, to reserve the humeral canal for future arthroplasty and to reduce time and cost of surgery.

In the following, further aspects of the stemless shoulder prosthesis as disclosed herein are described.

The prosthesis may be provided in different sizes to take the anatomical variety of the patients into account. The size of the wall sections may increase with increasing size of the prosthesis. However, according to one aspect the size of the base portion may remain constant, i.e. prostheses of different sizes are provided with a uni-sized base portion. This may apply for a symmetrical design having a circular base portion as well as for an anatomical design with a non-circular base portion, in particular having an egg-shaped or pear-shaped design.

Further embodiments of the disclosure are also recited in the dependent claims, the description and the drawings.

The different embodiments of the stemless shoulder prosthesis described above in accordance with the scope of the independent claim(s) and the features realized there and/or recited in the dependent claims of the disclosure may be combined.

Further areas of applicability of the present disclosure will become apparent from the detailed description provided hereinafter. It should be understood, that the detailed description and specific examples are intended for the purpose of illustration only and are not intended to limit the scope of the invention in any way. The figures are simplified and schematic. Details not necessary for the understanding of the invention are omitted.

The present disclosure will be explained in more detail and becomes fully understood from the detailed description and the accompanying drawings, wherein FIGS. 1 to 5 show an exemplary embodiment of a stemless shoulder prosthesis according to the present disclosure from various perspectives.

FIG. 1 shows a stemless shoulder prosthesis 10 according to the present disclosure having a symmetrical design. Prosthesis 10 comprises a circular base plate 11 provided with recesses 11' at its radially outer rim. Prosthesis 10 is connected to prosthetic humeral head 15.

The distal side of base plate 11 is provided with anchoring means 12 that serve to reliably anchor prosthesis 10 in the humerus bone of a patient. Anchoring means 12 comprise five wall sections 13 regularly disposed around a central axis C of prosthesis 10. Each wall section 13 comprises wall portions 13a, 13b which are at least partly arranged parallel to each other and which extend perpendicularly from base plate 11. Wall portions 13a, 13b are in essence planar. Wall portions 13a, 13b of each wall section 13 merge at a radially outer edge O of wall sections 13. At radially inner edges I of wall sections 13, wall portions 13b merge into wall portion 13a of neighboring wall sections 13 at transition zones T. Like the radially outer edges O, transition zones T have a rounded geometry.

The term "radially" is in this context to be understood to be related to a distance from central axis C. In other words, radially inner edge I is located closer to central axis C than radially outer edge O.

Transition zones T define in this exemplary embodiment the radially innermost points of anchoring means 12 thereby defining a free central space F around central axis C which is devoid of protrusions or wall elements. Therefore, in an implanted state of prosthesis 10, material of the humerus bone extends into space F promoting osseointegration. To foster this process, wall portions 13a, 13b of wall sections 13 are provided with openings 25 which—inter alia—improve the blood circulation in regions adjacent to prosthesis 10. In particular, openings 25 improve the blood circulation—and thus osseointegration—in a circumferential direction with respect to central axis C. Moreover, providing openings 25 and free central space F minimizes the size of prosthesis 10 within the bone thereby minimizing the surgical impact of the implant while at the same time promoting its osseointegration properties. It should be noted, however, that openings 25 are generally not mandatory.

To facilitate the insertion of prosthesis 10 into the bone of the patient, wall portions 13a, 13b and transition zones T are provided with a cutting edge 29 at their distal edges. Since wall portions 13a, 13b and transition zones T form together a star-like closed loop around central axis C, cutting edge 29 is also continuous.

The geometry of wall sections 13 is such that their distal edges essentially recede towards the radially inner end I of respective wall section 13. In the shown exemplarily embodiment, the distal edges of wall sections 13 are curved reaching their minimum at transition zones T adjacent radially inner edges I. However, a linear slope of said distal edges is also conceivable. As regards distal height, the minimum of anchoring means 12 is defined by transition zones T.

Figure 2:
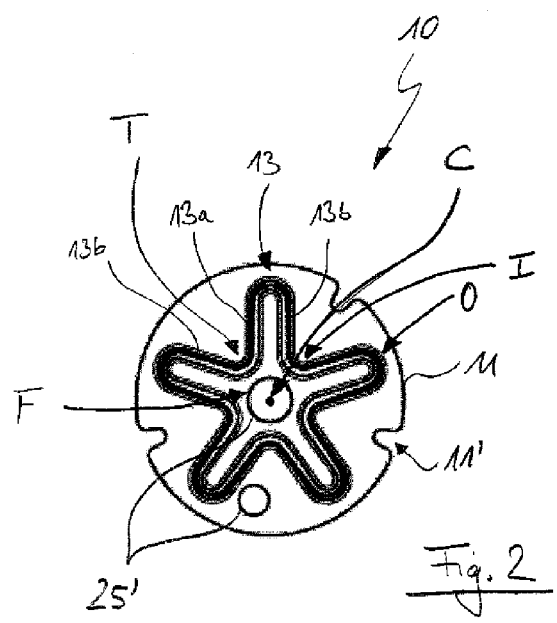

FIG. 2 shows a view of prosthesis 10 along central axis C from distal. This perspective reveals the geometry of anchoring means 12 defined by wall sections 13 resembling—figuratively speaking—a star with five arms having rounded transitional segments between the arms and rounded outer arm ends. It can further be seen that wall portions 13a, 13b of wall sections 13 extend at least is partially parallel to each other. However, in specific embodiments, it may be advantageous to arrange wall portions 13a, 13b inclined relative to each other and/or the number of wall sections 13 differs from this specific embodiment.

Further, it can be taken from FIG. 2, that base plate 11 is not only provided with recesses 11' but also comprises openings 25' which may e.g. serve to fix prosthesis 10 even more reliably to the humerus bone, e.g. by using a screw.

Figure 3:
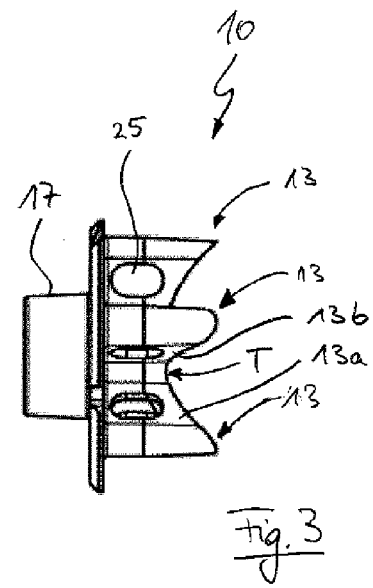
Figure 4:
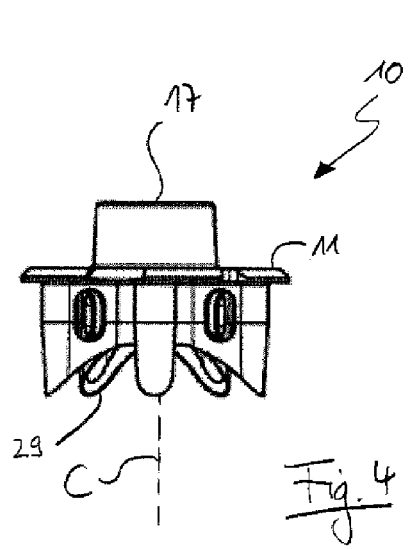
Figure 5:
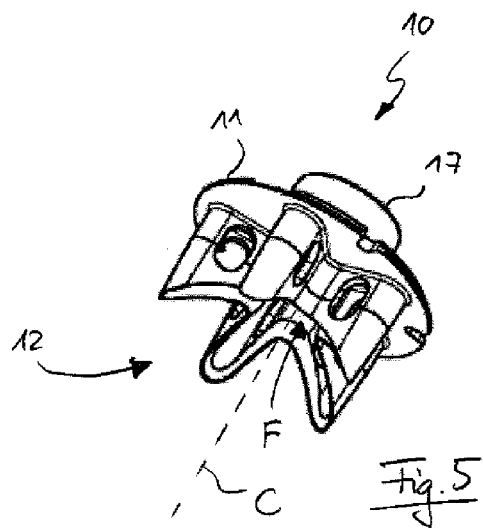

FIGS. 3 and 4 show different side views of prosthesis 10. Humeral head 15 is not attached to prosthesis 10. Therefore, a view on connection portion 17 is unobstructed. Connection portion 17 is slightly tapered towards proximal. Instead of a taper connection other types of connection means to reliably fix humeral head 15 to prosthesis 10 may be provided.

FIG. 5 shows prosthesis 10 again in a perspective view similar to that of FIG. 1 albeit without humeral head 15.

Unlike in the embodiment shown in the figures, the radially outwardly facing sides of wall sections 13 may be provided with protrusions such as small ribs or webs extending in a plane perpendicular to the central axis C.

All anatomical terms relating to directions and locations, such as anterior, posterior, medial, lateral, proximal, distal and sagittal, refer to an intended implanted state of the components and implants described above.

The description is merely of exemplary nature and, thus, variations that do not depart from the gist of the disclosed teachings are intended to be within the scope of the disclosure.

List of Reference Numbers
10 prosthesis
11 base plate
11' recess
12 anchoring means
13 wall section
13a, 13b wall portion
15 humeral head
17 connection portion
25, 25' opening
29 cutting edge
C central axis
F free central space
I radially inner edge
O radially outer edge
T transition zone

The invention claimed is:

1. Stemless shoulder prosthesis comprising a fixation device for fixing the prosthesis to a resected humerus bone, the fixation device comprising a base portion and anchoring means, the base portion having a distal side adapted to contact a resection plane of the bone and a proximal side for carrying a humeral head, and the anchoring means being connected to the distal side of the base portion and adapted to fix the prosthesis to the bone, wherein the anchoring means define a central axis perpendicular to the distal side of the base portion and a free central space around the central axis, wherein the anchoring means comprise wall sections projecting from the base portion substantially perpendicular to the distal side of the base portion, wherein each wall section includes a height, a length, and a width, and wherein the length is greater than the width and is measured between an inner and an outer edge of the wall section, wherein each wall section extends between the inner edge and the outer edge, and wherein the wall sections have the height measured from the distal side of the base portion, the height of each wall section decreasing along its length from its outer edge towards the inner edge, each wall section having a maximum height at its outer edge and a minimum height at its inner edge, wherein the wall sections form a wall extending around the free central space, wherein the wall extends around the free central space in a closed loop; and wherein the length of each wall section extends radially such that its outer edge meets the outer edge of a first adjacent wall section, and its inner edge meets the inner edge of a second adjacent wall section.

2. Stemless shoulder prosthesis according to claim 1, wherein the wall sections are arranged around the free central space and are in particular evenly distributed.

3. Stemless shoulder prosthesis according to claim 1, wherein the wall defines alternating radially outer convex wall portions and radially inner concave wall portions as the wall extends around the free central space.

4. Stemless shoulder prosthesis according to claim 1, wherein the outer edge of each wall section is rounded.

5. Stemless shoulder prosthesis according to claim 1, wherein each wall section is formed by two wall portions merging into one another at the outer edge of the wall section and each wall portion of a wall section merging into a wall portion of a neighboring wall section at a common transition zone.

6. Stemless shoulder prosthesis according to claim 5, wherein the wall portions of each wall section extend at least partially parallel to each other.

7. Stemless shoulder prosthesis according to claim 5, wherein each transition zone is rounded.

8. Stemless shoulder prosthesis according to claim 5, wherein each wall section has a minimum height at the common transition zone.

9. Stemless shoulder prosthesis according to claim 1, wherein each wall section comprises a distal edge which is formed at least partly as a cutting edge.

10. Stemless shoulder prosthesis according to claim 1, wherein at least one of the wall sections and/or the base portion comprises at least one opening.

11. Stemless shoulder prosthesis according to claim 1, wherein the base portion comprises a plate.

* * * * *